(12) United States Patent
Kim et al.

(10) Patent No.: US 7,754,252 B2
(45) Date of Patent: Jul. 13, 2010

(54) GINSENG FERMENTED BY LACTIC ACID BACTERIUM, YOGHURT CONTAINING THE SAME, AND LACTIC ACID BACTERIA USED IN THE PREPARATION THEREOF

(75) Inventors: Dong Hyun Kim, Seoul (KR); Myung Joo Han, Seoul (KR); Min Kyung Choo, Seoul (KR)

(73) Assignee: Kuan Industrial Co., Ltd., Seoul (KR)

( * ) Notice: Subject to any disclaimer, the term of this patent is extended or adjusted under 35 U.S.C. 154(b) by 1097 days.

(21) Appl. No.: 10/536,791

(22) PCT Filed: Nov. 29, 2003

(86) PCT No.: PCT/KR03/02609

§ 371 (c)(1),
(2), (4) Date: Dec. 21, 2005

(87) PCT Pub. No.: WO2004/050892

PCT Pub. Date: Jun. 17, 2004

(65) Prior Publication Data

US 2006/0127379 A1 Jun. 15, 2006

(30) Foreign Application Priority Data

Dec. 5, 2002 (KR) .................. 10-2002-0077081

(51) Int. Cl.
*A61K 36/254* (2006.01)
*A61K 36/258* (2006.01)
*A23C 9/12* (2006.01)
*A23C 17/00* (2006.01)

(52) U.S. Cl. .................. 424/728; 426/34; 426/39; 426/43

(58) Field of Classification Search .................. None
See application file for complete search history.

(56) References Cited

U.S. PATENT DOCUMENTS 4,702,923 A 10/1987 Tokumaru et al.
5,776,460 A * 7/1998 Kim et al. .................. 424/728

FOREIGN PATENT DOCUMENTS

CN 1330870 1/2002
JP 6321643 * 9/1988
JP H05-84065 4/1993
KR 1982-0000919 5/1982
KR 1988-0000073 3/1998
KR 2003-0037005 5/2003
WO WO 96/37113 11/1996

OTHER PUBLICATIONS

Eun-Ah Bae, Myung Joo Han, Min-Kyung Choo, Sun-Young Park and Dong-Hyun Kim, "Metabolism of 20(S)- and 20(R)-Ginsenoside Rg3 by Human Intestinal Bacteria and Its Relation to in Vitro Biological Activities", Biol. Pharm. Bull. 25(1) 58-63, 2002.

Eun-Ah Bae, Min-Kyung Choo, Eun-Kyung Park, Sun-Young Park, Ho-Young Shin, and Dong-Hyun Kim, "Metabolism of Ginsenoside Rc by Human Intestinal Bacteria and Its Related Antiallergic Activity" Biol. Pharm. Bull. 25(6) 743-747, 2002.

Hye-Young Park, Eun-Ah Bae, Myung Joo Han, Eung-Chil Choi and Dong-Hyun Kim, "Inhibitory of *Bifidobacterium* Spp. Isolated from a Healthy Korean on Harmful Enzymes of Human Intestinal Microflora", Arch. Pharm. Res. vol. 21, No. 1, pp. 54-61, 1998.

Hideo Hasegawa and Ikuko Saiki, "Biotransformation of Intestinal Bacterial Metabolites of Ginseng Saponin to Biologically Active Fatty-acid Conjugates", Advances in Ginseng Research 2002, Proceedings of the 8$^{th}$ International Symposium on Ginseng, Seoul, Korea, Oct. 28-31, 2002, The Korean Society of Ginseng, pp. 317-334.

Ikuko Saiki, "Anti-metastatic Effect of Ginseng Saponins and its Molecular Mechanism", Advances in Ginseng Research 2002, Proceeding of the 8$^{th}$ International Symposium on Ginseng, Seoul, Korea, Oct. 28-31, 2002, The Korean Society of Ginseng, pp. 305-316.

Chisato Wakabayashi, Hideo Hasegawa, Jun Murata and Ikuo Saiki, "In Vivo Antimetastatic Action Of Ginseng Protopanaxadiol Saponins Is Based on Their Intestinal Bacterial Metabolites After Oral Administration", Research Institute For Wakan-Yaku, Toyama Medical and Pharmaceutical University, pp. 411-417. 1998.

* cited by examiner

*Primary Examiner*—Michele Flood
*Assistant Examiner*—Catheryne Chen
(74) *Attorney, Agent, or Firm*—Blakely, Sokoloff, Taylor & Zafman LLP

(57) ABSTRACT

This invention relates to lactic fermenting products of ginseng obtained by fermentation of ginseng using lactic acid bacteria, yoghurt containing said lactic fermenting products of ginseng, and lactic acid bacteria used in the preparation of said lactic fermenting products of ginseng.

5 Claims, No Drawings

GINSENG FERMENTED BY LACTIC ACID BACTERIUM, YOGHURT CONTAINING THE SAME, AND LACTIC ACID BACTERIA USED IN THE PREPARATION THEREOF

CROSS-REFERENCE TO OTHER APPLICATIONS

This is a National Phase of International Application No. PCT/KR2003/002609, filed on Nov. 29, 2003, which claims priority from Korean Patent Application No. 10-2002-0077081, filed on Dec. 5, 2002.

TECHNICAL FIELD

This invention relates to lactic fermenting products of ginseng obtained by fermentation of ginseng using lactic acid bacteria, yoghurt containing said lactic fermenting products of ginseng, and lactic acid bacteria used in the preparation of said lactic fermenting products of ginseng.

BACKGROUND OF THE INVENTION

Ginseng is a perennial plant belonging to the genus of Ginseng, the family of Araliaceae in the classification of the plant. About eleven kinds of ginseng have yet been known on the earth. The representative species of ginseng include *Panax ginseng* C. A. Meyer which grows naturally in the area of far-east Asia at 33° through 48° North Latitude (Korea, Northern Manchuria, an area of Russia) and which has excellent pharmaceutical effects; *Panax quinquefolium* L. which grows naturally or has been cultivated in the United States and Canada; *Panax notoginseng* F. H. which grows naturally or has been cultivated in China (the south-eastern area of Yunnan province and the south-western area of Guangxi province); and *Panax japonicus* C. A. Meyer which ranges widely in the area of Japan, the south-eastern China and Nepal.

Ginseng was classified as a top grade in plant efficacy by SINON HERBAL (Shen Nong Ben Cao Jing, called in China), the earliest herbal in China, and has been used as a valuable restorative for a long time. From many pharmacological experiments, it is demonstrated that ginseng strengthens the non-specific resistance of a human body in respect to the stress and also has an anti-acidic action. It has also been clarified that ginseng has other pharmacological effect such as improving hypertension, strengthening insulin action, lowering blood sugar level in Alloxan diabetic mouse, hepatic RNA synthesis in white rat, promoting protein synthesis and sugar and lipid metabolism together with an anti-tumor effect.

In Asian countries of Korea, China and Japan, ginseng has been used as a natural medicine for treating various diseases such as mental diseases, disorders in nervous system and diabetes. Saponin, a principal active component of ginseng, has been known as having the effect of strengthening robustness or stamina, sedation and anti-hypertension.

At the present time, ginseng is used in form of white ginseng processed by drying crude ginseng from the cultivated at ambient temperature, red ginseng processed by heating crude ginseng (green ginseng) at 98 to 100° C., or super red ginseng prepared by heating crude ginseng at 120 to 180° C.

On the other hand, ginseng root contains about 4 to 10% of ginseng saponin (e.g., *Panax ginseng* C. A. Meyer contains 4 to 8% of ginseng saponin, and *Panax quinquefolium* L. contains 4 to 10% of ginseng saponin). Said ginseng saponin refers to a mixture of various ginsenosides. In particular, *Panax ginseng* C. A. Meyer contains relatively high content of ginsenoside Rb1, Rc and Rg1, and *Panax quinquefolium* L. contains relatively high content of ginsenoside Rb1 and Re.

Specific type of ginsenoside included in ginseng and their pharmacological effects are shown in the following Table 1.

TABLE 1

| Type of Ginsenoside | Effect |
|---|---|
| Ginsenoside-Rb1 | Suppression of central nerve with sedation, Suppression of central nervous voracity, Suppression of aggressive movement, Alleviation of pain, Anti-convulsion, Anti-apprehension, Accelerating secretion of adrenal cortex stimulating hormone and corticosteron, Promoting bio-synthesis of cholesterol, Improvement of memory, Lowering hyper-cholesterol, neutral fat and free aliphatic acid, Accelerating subsistence of nerves cells, Protection from liver damage, Accelerating synthesis of DNA, RNA, protein and lipid in marrow cells, Accelerating acetylcholin release, Vasodilation, Suppression of agglutination of thrombocytes, Suppression of lipid peroxidation, Promoting cholesterol metabolism, Anti-inflammation, Activation of voracity function, Suppression of hypertrophy of glomerulus. |
| Ginsenoside-Rb2 | Accelerating sugar and fat metabolism, Anti-diabetic action, Controlling equilibrium of fat metabolism, Accelerating protein and fat synthesis, Lowering hyper-cholesterol and preventing arteriosclerosis, Antagonism on cancer toxin hormone, Suppression of proliferation of smooth muscle cells, Accelerating secretion of adrenal cortex stimulating hormone and corticosteron, DNA, RNA, Improvement of stressful decrease of appetite, Suppression of generation of tumoral vessel, Accelerating production of anti-peroxidative substance, Activation of ATP supply in liver tissues, Adjustment of immunity, Promoting cholesterol metabolism, Proliferation of liver cells and Acceleration of DNA synthesis, Suppression of agglutination of thrombocytes, and Alleviation. |
| Ginsenoside-Rc | Accelerating synthesis of RNA, serum cholesterol in liver, Accelerating synthesis of DNA, RNA, protein and lipid in marrow cells, Pain alleviation. Accelerating secretion of corticosteron, Promoting bio-synthesis of prostacycline and Suppression of hypertrophy of glomerulus. |
| Ginsenoside-Rd | Accelerating secretion of adrenal cortex stimulating hormone and corticosteron, Suppression of the hypertrophy of glomerulus. |
| Ginsenoside-Re | Accelerating secretion of adrenal cortex stimulating hormone and corticosteron, Alleviation of pain, Vasodilation, Anti-high temperature stress, Suppression of the proliferation of smooth muscle cells, Accelerating synthesis of DNA, RNA, protein |

TABLE 1-continued

| Type of Ginsenoside | Effect |
|---|---|
| | and lipid in marrow cells, Protection from liver damage, and Promoting cholesterol metabolism. |
| Ginsenoside-Rg1 | Strengthening immune function, Suppression of agglutination of thrombocytes, Anti-thrombin, Activation for the efficiency, Increasing an ability of memory and study, Anti-fatigue, Anti-stress, Excitation of central nerve, Vasodilation, Anti-inflammation, Anti-nephritis and functioning as a agent to increase the amount of blood stream in kidney, Function to protect from the injurious stimulation like high temperature circumstance and heat resistant-pyrogenic substance, Improvement of stressful lesion of slow motion, Accelerating subsistence of nerves cells, Proliferation of liver cells and Acceleration of DNA synthesis, Accelerating secretion of adrenal cortex stimulating hormone, Promoting cholesterol metabolism and Protection from liver damage. |
| Ginsenoside-Rh1 | Suppression of experimental liver damage, Promotion of differentiation of tumoral cells, Suppression of agglutination of thrombocytes, Anti-inflammation and Anti-allergy. |
| Ginsenoside-Rh2 | Suppression of cancer cell proliferation, Inducing re-differentiation of cancer cell, Suppression of permeation of cancer cells, Suppression of tumor proliferation, Increasing anti-cancer activity of an anti-cancer medicine, Anti-allergy. |
| Compound K | Suppressing significant generation of tumoral vessel and spread of cancer cell, Blocking secretion of IV type collagenase, Activating to form anti-regeneration vessel, and Suppressing agglutination of thrombocytes, Anti-allergy and Anti-inflammation. |

It has been found that the principal active components responsible for pharmacological effects of ginseng are saponins such as ginsenoside Rb1, Rb2 and Rc. However, the active materials substantially having anti-tumor activities, capacities for suppressing metastasis of cancer cells, and/or anti-allergic effects include saponins such as Compound K (20-0-β-D-glucopyranocyl-20(S)-protopanaxidiol) as a intestinal-bacterial fermenting product, ginsenoside Rh1 and Rh2 and $\Delta^{20}$-ginsenoside Rh2, but these saponins are contained in ginseng in extremely small amount.

Accordingly, it is necessary to increase amounts of saponins such as Compound K, ginsenoside Rh1 and Rh2 and $\Delta^{20}$-ginsenoside Rh2 (i.e. the mixture of ginsenoside Rk2 and ginsenoside Rh3) as present at extremely lower level in the crude ginseng, in order to improve anti-cancer activities, anti-allergic effects and reinforcement of immune activity in human bodies by pharmacological effects of ginseng.

SUMMARY OF THE INVENTION

Thus, the inventors have also made attempts to more efficiently obtain saponins such as Compound K, ginsenoside Rh1 and Rh2, and $\Delta^{20}$-ginsenoside Rh2. As a result, the inventors has found that lactic fermenting products of ginseng obtained by fermentation of ginseng using lactic acid bacteria contain significantly more amounts of Compound K, ginsenoside Rh1 and Rh2, and Δ20-ginsenoside Rh2. The present invention is based on such findings.

Accordingly, it is one object of the invention to provide lactic fermenting products of ginseng.

Further, it is other object of the invention to provide yoghurts containing said lactic fermenting products of ginseng.

Further, it is another object of the invention to provide lactic acid bacteria used for the preparation of said lactic fermenting products of ginseng.

DETAILED DESCRIPTION OF THE INVENTION

According to the invention, (1) lactic fermenting products of ginseng, (2) yoghurts containing said lactic fermenting products of ginseng, and (3) lactic acid bacteria advantageously used for the preparation of said lactic fermenting products of ginseng, are provided.

The invention is described more specifically here in below.

According to the invention, when ginseng is fermented by lactic acid bacteria, the saponin ingredients of ginseng prior to fermentation are to be bio-converted to the saponin ingredients of Compound K(20-O-β-D-glucopyranocyl-20(S)-protopanaxadiol), ginsenoside Rh1 and ginsenoside Rh2, and $\Delta^{20}$-ginsenoside Rh2 which were not included at all or included infinitesimally in said ginseng prior to the fermentation. Then, lactic fermenting products of ginseng comprise at least one ingredient selected from the group consisting of Compound K(20-O-β-D-glucopyranocyl-20(S)-protopanaxadiol), ginsenoside Rh1 and ginsenoside Rh2, and $\Delta^{20}$-ginsenoside Rh2.

According to general knowledge in the relevant art, the saponin ingredients of Compound K, ginsenoside Rh1 and Rh2, and $\Delta^{20}$-ginsenoside Rh2 have more excellent activity of anti-cancer and anti-allergy or suppressing cancer spread as compared with the same of ginsenoside Rb1, Rb2 and Rc (see the literatures of "Bae et. al., Biol. Pharm. Bull., 25, 743-747, 2002; Bae et al., 25, 58-63, 2002; Wakabayashi et al., Oncol. Res., 9, 411-417, 1998; Saiki et. al., Proceedings of the 8th international symposium on Ginseng (Korea Ginseng Academy, Seoul, Korea), 305-316, 2002; Hasegawa and Saiki, Proceedings of the 8th international symposium on Ginseng (Korea Ginseng Academy, Seoul, Korea), 317-334, 2002).

On the other hand, sources of ginseng which can be used for the fermentation by lactic acid bacterium are not particularly limited and the Korean ginseng (*Panax ginseng* C. A. Meyer) as well as other kinds of ginsengs such as *Panax quinquefolium* L., *Panax Notoginseng* F. H. Chen and *Panax japonicus* C. A. Meyer in their natural form or their processed product can be employed. More specifically, either at least one of the ginseng leaf, ginseng extract and ginseng powder, or green ginseng, red ginseng, white ginseng and other kinds of ginsengs afore-mentioned (hereinafter inclusively referred to as "ginseng") can be employed. In terms of processing, the treatment with acid, at high temperature and under pressure can be desirably applied to give lactic fermenting products of ginseng.

Pulverizing degree of ginseng in a form of dried powder is not particularly restricted. Ginseng can be pulverized so that lactic acid bacterium may penetrate very effectively into tissues or fibrous cells of ginseng. Such pulverizing degree of ginseng and other pulverization method has been commonly known to a person in the pertinent art. Though the treatment with acid, at high temperature and pressure can be readily applied to a product per se, it is preferable to adopt the treatment of dry pulverization in consideration of the effect of the treatment and the fermantation efficiency thereafter.

Pulverizing degree of ginseng in the dry pulverization is not particularly restricted too.

In the case that at least one pulverized ginseng material selected from the group consisting of the green ginseng, red ginseng, white ginseng, fine ginseng, *Panax quinquefolium* L., ginseng lief, ginseng extract and ginseng powder (hereinafter, "the ginseng source") is fermented by lactic acid bacterium, the amount of Compound K is particularly increased in the product of ginseng fermented by lactic acid bacterium.

The ginseng product by acid treatment can be obtained by adding an acid, preferably acetic acid, lactic acid, citric acid, butyric acid, tartaric acid, propionic acid or hydrochloric acid to at least one pulverized ginseng material selected from the group consisting of the green ginseng, red ginseng, white ginseng, fine ginseng, *Panax quinquefolium* L., ginseng leaf, ginseng extract and ginseng powder and cultivating the mixture at 60° C. for 5 hours and then neutralizing with calcium salt. According to the invention, in the case that ginseng treated with an acid is fermented by lactic acid bacterium, the amounts of ginsenoside Rh1 and Rh2 are particularly increased in the resultant fermenting products by lactic acid bacterium.

The ginseng product can be prepared by treating ginseng at high temperature, e.g., red ginseng can be prepared by heating said pulverized ginseng material at 100° C. for 2 to 5 hours. According to the invention, in case that ginseng treated at high temperature is fermented by lactic acid bacterium, the amounts of Compound K and ginsenoside Rh1 and Rh2 are particularly increased in the resultant fermenting products by lactic acid bacterium.

The ginseng treated under pressure can be prepared by treating said pulverized ginseng material under pressure at 110 to 130° C. for 2 to 5 hours. According to the invention, in case that ginseng treated under pressure is fermented by lactic acid bacterium, the amounts of ginsenoside Rh1 and Rh2 and $\Delta^{20}$-ginsenoside Rh2 are particularly increased in the resultant lactic fermenting products of ginseng despite the low amount of Compound K.

On the other hand, the method for preparing lactic fermenting products of ginseng is not particularly limited and can be carried out by a method employed generally in the pertinent art under the proper condition for the fermentation with lactic acid bacterium.

Specifically, lactic fermenting products of ginseng can be prepared through the suspension of the pulverized ginseng material in water for lactic acid bacterium to be cultured at suitable temperature for 48 to 72 hours and passing through a process of bio-converting for the resultant lactic fermenting products of ginseng, centrifuging the resultant product and then filtrating the upper transparent liquid only and concentrating the liquid to give lactic fermenting products of ginseng.

The lactic acid bacterium used for the fermentation is not particularly limited, as long as the bio-converting rate to Compound K, ginsenoside Rh1 and Rb2, and $\Delta^{20}$-ginsenoside Rh2 is high. For instance, bacteria of *Lactobacillus, Streptococcus* or *Bifidobacterium* spp. can be used. More specifically, at least one of *Bifidobacterium* K-103 (see Arch. Pharm. Res., 21, 54-61, 1998, Professor Dong-Hyun, Kim, the college of pharmacy, Kyung-Hee University, Seoul, Korea), *Bifidobacterium* K-506 (see Arch. Pharm. Res., 21, 54-61, 1998, Professor Dong-Hyun, Kim, the college of pharmacy, Kyung-Hee University, Seoul, Korea), *Bifidobacerium cholerium* KK-1 (KCCM-10364), *Bifidobacterium minimum* KK-2 (KCCM-10365), *Bifidobacterium* H-1 (KCCM-10493) and *Bifidobacterium* KK-11 (Professor Dong-Hyun, Kim, the college of pharmacy, Kyung-Hee University) can be employed.

Among these, *Bifidobacterium* H-1, *Bifidobacterium cholerium* KK-1 and *Bifidobacterium minimum* KK-2 are the microorganisms which have been firstly developed by the inventors to obtain lactic fermenting products of ginseng. Said *bifadobacterium cholerium* KK-1, *Bifidobacterium minimum* KK-2 and *Bifidobacterium* H-1 have been deposited respectively as the Accession numbers of KCCM-10364 (Mar. 22, 2003), KCCM-10365 (Mar. 22, 2003), KCCM-10493 (May 1st, 2003) with the Korean Culture Center of Microorganism. *Bifidobacterium cholerium* KK-1 and *Bifidobacterium minimum* KK-2, *Bifidobacterium* H-1 and *Bifidobacterium* K-11 of the invention are gram positive and anaerobic, and also fructose 6-phosphate phosphoketolase positive.

The bacilli have the sugar usability as shown in the following table.

| CLASS | Sugar Usability | | | |
|---|---|---|---|---|
| | *Bifidobacterium* KK-1 | *Bifidobacterium* KK-2 | *Bifidobacterium* H-1 | *Bifidobacterium* KK-11 |
| amigladin | − | − | − | − |
| arabinose | − | +/− | + | + |
| cellobiose | − | +/− | − | − |
| dextrin | + | + | − | − |
| esculin | − | − | +/− | +/− |
| fructose | − | + | + | +/− |
| galactose | + | + | + | + |
| gluconate | − | − | − | − |
| glucose | +/− | + | + | + |
| glycogen | +/− | + | − | − |
| inositol | − | − | − | − |
| inulin | − | +/− | +/− | +/− |
| lactose | + | +/− | + | + |

-continued

| CLASS | Sugar Usability | | | |
| --- | --- | --- | --- | --- |
| | Bifidobacterium KK-1 | Bifidobacterium KK-2 | Bifidobacterium H-1 | Bifidobacterium KK-11 |
| maltose | +/− | + | + | + |
| mannitol | − | + | + | + |
| mannose | +/− | + | + | + |
| melezitose | − | − | − | − |
| melibiose | + | − | + | + |
| raffinose | + | − | + | + |
| ribose | +/− | +/− | +/− | +/− |
| salicin | + | + | + | + |
| sorbitol | +/− | − | − | − |
| starch | + | + | − | − |
| sucrose | − | +/− | + | + |
| trehalose | − | − | − | − |
| xylose | − | +/− | + | + |

Said Bifidobacteria KK-1, KK-2, H-1 and K-11 are characteristically identical with the other bacterium of the same species in the classification. However, the Bifdobacteria enables to provide lactic fermenting products of ginseng thereby which includes much higher amount of Compound K, ginsenoside Rh1 and Rh2, and a $\Delta^{20}$-ginsenoside Rh2, when applied to the processes for fermentation of ginseng.

Accordingly, the lactic fermenting products of ginseng of the prevent invention contains much higher amount of Compound K, ginsenoside Rh1 and Rh2, and $\Delta^{20}$-ginsenoside Rh2. Particularly, it is preferable that the whole amount of (Compound K+ ginsenoside Rh1), (ginsenoside Rh1+ginsenoside Rh2), (ginsenoside Rh2+$\Delta^{20}$-ginsenoside Rh2+ginsenoside Rh1) or (Compound K+ginsenoside Rh1+ginsenoside Rh2) be included respectively in the ratio of more than 0.1 with respect to total amount of (ginsenoside Rc+ginsenoside Rd+ginsenoside Rb1+ginsenoside Rb2+ginsenoside Re+ginsenoside Rg1). It is further preferable that the ratio of the both components be in the range of 1:50 to 50:1 in case of the production of (Compound K+ginsenoside Rh1) and 50 to 50:1 in case of the production of (ginsenoside Rh2+ginsenoside Rh1) and that the ratio of the sum of (ginsenoside Rh2+$\Delta^{20}$-ginsenoside Rh2): ginsenoside Rh1 be in the range of 1:50 to 50:1 in case of the production of (ginsenoside Rh2+A 20-ginsenoside Rh2+ginsenoside Rh1) and the ratio of Compound K: ginsenosides be in the range of 1:50 to 50:1 in case of the production (Compound K+ginsenoside Rh1+ginsenoside Rh2). Not included naturally in red ginseng, Compound K appears increasingly in red ginseng, when fermented by lactic acid bacterium according to the invention.

Said lactic acid bacteria of the invention appear to suppress the intestine-harmful-*bacillus* and/or to suppress the activity of the intestine-harmful-enzyme and/or to suppress the proliferation of cancer cells.

On the other hand, the invention provides also a ginseng yoghurt containing the resultant substance of the fermentation by lactic acid bacterium.

As said ginseng yoghurt contains the resultant lactic fermenting products of ginseng according to the invention, namely, includes plenty of the ginseng saponin ingredients of Compound K, ginsenoside Rh1 and Rh2, and $\Delta^{20}$-ginsenoside Rh2, the yoghurt of the invention is certainly a multifunctional yoghurt to exert the high physiological function of Compound K, ginsenoside Rh1 and Rh2, and $\Delta^{20}$-ginsenoside Rh2, more specifically the functions of anti-cancer, anti-allergy and the reinforcement of immunity. Such ginseng yoghurt can be prepared by merely adding 0.1 to 10% by weight of said resultant lactic fermenting products of ginseng to a usual yoghurt. However, this method requires separately a process for the fermentation of milk of yoghurt and another process for the additive fermentation of ginseng by lactic acid bacterium to obtain lactic fermenting products of ginseng. Thus, this method is not industrially favorable for economic reasons. Accordingly, the ginseng yoghurt of the invention can be prepared by fermenting concurrently milk of yoghurt and 0.1 to 10% by weight of ginseng by lactic acid bacterium. In the reactant for the fermentation, the vitamins can be included.

The bacterium to prepare a ginseng yoghurt is not particularly limited, if enabling to ferment concurrently both ginseng and milk for the preparation of yoghurt. For instance, the bacterium of *Lactobacillus, Streptococcus bacillus* or *Bifidobacterium*, preferably at least one selected from the group of *Bifidobacterium* K-103, *Bifidobacterium* K-506, *Bifidobacterium cholerium* KK-1, *Bifidobacterium minimum* KK-2, *Bifidobacterium* H-1 and *Bifidobacterium* KK-11 can be used.

Milk for preparing yoghurt is not particularly restricted, and goat milk, sheep milk, nonfat milk, skim milk as well as cow milk can be used.

After the fermentation to prepare a yoghurt, lactic acid bacterium is optionally removed. However, as lactic acid bacterium has a favorable function to improve the intestinal conditions, it is preferable not to remove said lactic acid bacterium. Accordingly, the yoghurt of the invention can improve the intestinal conditions.

On the other hand, the ginseng powder yoghurt can be available by adding ginseng powder to the resultant yoghurt. Accordingly, the yoghurt is not particularly limited to a formal class. Then, various types of usual yoghurt prepared through the fermentation of milk by lactic acid bacterium can be possible.

The invention will be understood more readily with reference to the following examples, however, these examples are intended to illustrate the invention only and are not to be construed to limit the scope of the invention. The modification and application thereof usually acceptable in the pertinent art fall within the scope of the invention.

THE PREFERRED EMBODIMENTS OF THE INVENTION

Example A1

Undried ginseng root (5-year *P. ginseng* C. A. Meyer root from Kumsan in Korea procured from Kyungdong Market) was washed thoroughly with hot water, dried and ground to a fine powder. Subsequently 1 g of powdered dry ginseng prepared as described above and 0.1 g of vitamin C were suspended in 100 ml of milk. Yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A2

Each 2 g of powdered dry ginseng prepared from sufficiently dehydrated undried ginseng root or the root hair of ginseng and 0.1 g of vitamin C were suspended in 100 ml of milk. Yogurt was then obtained by inoculating each 1 ml (about $10^9$ cells/ml) of precultivated *Bifidobacterium* K-103 and *Bifidobacterium* K-506 thereto, followed by a fermentation for 24 hrs at 37° C.

Example A3

1 g of powdered dry ginseng prepared from sufficiently dehydrated undried ginseng root and 0.1 g of vitamin C were suspended in 100 ml of milk. Yogurt was then obtained by inoculating each 1 ml (about $10^9$ cells/ml) of precultivated *Lactobacillus bulgaricus, Streptococcus thermophilus, Bifidobacterium* KK-1 and *Bifidobacterium* KK-2 thereto, followed by a fermentation for 12 hrs at 37° C.

Example A4

1 g of powdered dry white ginseng root and 0.1 g of vitamin C were suspended in 100 ml of milk. Yogurt was then obtained by inoculating each 1 ml (about $10^9$ cells/ml) of precultivated *Lactobacillus bulgaricus, Streptococcus thermophilus* and *Bifidobacterium* KK-1 thereto, followed by a fermentation for 24 hrs at 37° C.

Example A5

1 g of powdered dry ginseng root and 0.1 g of vitamin C were suspended in 100 ml of milk. Ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A6

Powdered dry ginseng root was treated with 0.5% lactic acid at 60° C. for 5 hrs followed by a neutralization and drying. 1 g of powdered dry ginseng root (acid-treated ginseng) prepared as described above and 0.1 g of vitamin C, were suspended in 100 ml of milk. Acid-treated ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A7

Powdered dry ginseng root was suspended in distilled water and steamed at 100° C. for 2 hrs followed by a drying. 1 g of powdered dry ginseng root (ginseng treated at high temperature) prepared as described above and 0.1 g of vitamin C were suspended in 100 ml of milk. high temperature treated ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A8

Powdered dry ginseng root was pressurized for 2 hrs at 120° C. followed by a drying. 1 g of powdered dry ginseng root (pressurized ginseng) prepared as described above and 0.1 g of vitamin C were suspended in 100 ml of milk. Pressurized ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A9

1 g of powdered dry ginseng root and 0.1 g of vitamin C were suspended in 100 ml of milk. Ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A10

Powdered dry ginseng root was treated with 5% lactic acid at 60° C. for 5 hrs followed by a neutralization and drying. 1 g of powdered dry ginseng root (high temperature treated ginseng) prepared as described above and 0.1 g of vitamin C were suspended in 100 ml of milk. high temperature treated ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A11

Powdered dry ginseng root was suspended in distilled water and steamed at 100° C. for 2 hrs followed by a drying. 1 g of powdered dry ginseng root (ginseng treated at high temperature) prepared as described above and 0.1 g of vitamin C were suspended in 100 ml of milk. high temperature treated ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Example A12

Powdered dry ginseng root was pressurized at 120° C. for 2 hrs followed by a drying. 1 g of powdered dry ginseng root (pressurized ginseng) prepared as described above and 0.1 g of vitamin C were suspended in 100 ml of milk. Pressurized ginseng yogurt was then obtained by inoculating each 1 ml (about $10^9$ cells/ml) of precultivated *Bifidobacterium* KK-1 and *Bifidobacterium* KK-2 thereto, followed by a fermentation for 24 hrs at 37° C.

Examples A13-A24

Each of lactic acid bacteria-fermented products was obtained by repeating exactly the same process as examples A1 to A12 above, except 2 g (wet weight) of precultivated lactic acid bacteria and 100 ml of distilled water instead of 100 ml of milk were used.

Experimental Example A1

Amount Analysis of Saponin Component 1 g of commercially available regular ginseng root (Nonghyup 4-6 year *P. ginseng* C. A. Meyer root from Kumsan in Korea procured from Kyungdong Market) and each 1 g of its powdered dry, acid-treated, high temperature treated and pressurized version (prepared by the same process as in examples above) was individually mixed with 100 ml of milk containing 0.1 g of Vitamin C. Each of the above mixture was subsequently innoculated with 1 g of *Bifidobacterium* KK-1 and *Bifidobacterium* KK-2, and fermented for 72 hrs at 37° C., followed by a concentration by decompression to obtain fermented yogurt of ginseng, high temperature treated ginseng, acid-treated ginseng and pressurized ginseng, respectively. Subsequently, 2 g of ginseng and each 2 g of its powdered dry, acid-treated, high temperature treated and pressurized version, and each 2 g of fermented products above were extracted with 100 ml of methanol 3 times. Each of the extracts was then concentrated and suspended in water followed by a extraction with 100 ml of ether 3 times. Each of the ether fractions was further extracted with 100 ml of butanol 3 times. The butanol fractions were then subject to concentration and subsequent TLC analysis after dissolved in methanol (Solvent system: $CHCl_3:MeOH:H_2O=65:35:10/CHCl_3:EtOAc:MeOH:H_2O=15:40:22:9$; Spraying reagent: 5% sulfuric acid in methanol; TLC scanner: Shimadzu CS-9301PC). The results obtained are shown in Table 2. The amount of each component was calculated based on which is contained in 100% of the finally extracted fraction.

Similar results as in Table 2 were also obtained with examples A1 to A4 and A9 to A12. Fermented ginseng yogurts according to Examples A13 to A24 were shown to contain similar amount of saponin to that of fermented yogurts as described above.

TABLE 2

| Name of the components | amount of component (%) | | | |
|---|---|---|---|---|
| | Ginseng (example A5) | fermented yogurt of ginseng (example A5) | high temperature treated ginseng (example A7) | fermented yogurt of high temperature treated ginseng (example A7) |
| ginsenoside Rb1 | 15.1 | 1.6 | 5.1 | 2.7 |
| ginsenoside Rb2 | 8.2 | 1.1 | 3.5 | 2.1 |
| ginsenoside Rc | 9.5 | 0.5 | 3.8 | 2.9 |
| ginsenoside Re | 10.7 | 2.7 | 7.8 | 4.5 |
| ginsenoside Rg3 | <1 | <1 | 14.6 | 8.5 |
| 20-ginsenoside Rg3 | <1 | <1 | 4.5 | <1 |
| compound K | 0 | 28.6 | <1 | 2.9 |
| ginsenoside Rh2 | <1 | <1 | <1 | 3.2 |
| $\Delta^{20}$-ginsenoside Rh2 | <1 | <1 | <1 | <1 |
| ginsenoside Rh1 | <1 | 1.2 | 0.5 | 1.8 |
| Protopanaxadiol | <1 | 2.1 | <1 | 2.1 |

| Name of the components | amount of component (%) | | | |
|---|---|---|---|---|
| | acid-treated ginseng (example A6) | fermented yogurt of acid-treated ginseng (example A6) | pressurized ginseng (example A8) | fermented yogurt of pressurized ginseng (example A8) |
| ginsenoside Rb1 | 2.5 | 1.2 | 2.5 | 1.2 |
| ginsenoside Rb2 | 2 | 0.9 | 1.2 | 0.8 |
| ginsenoside Rc | 1.8 | 1.1 | 1.5 | 1.0 |
| ginsenoside Re | 6.8 | 5.2 | 3.9 | 2.9 |
| ginsenoside Rg3 | 25 | 7 | 16.1 | 4.5 |
| 20-ginsenoside Rg3 | <1 | <1 | 6.5 | 2.1 |
| compound K | 0 | 2.2 | 0 | 1.2 |
| ginsenoside Rh2 | 0.2 | 10.2 | <1 | 4.5 |
| $\Delta^{20}$-ginsenoside Rh2 | 0.1 | 1.8 | <1 | 3.8 |
| ginsenoside Rh1 | 0.5 | 2.1 | 2.1 | 2.5 |
| protopanaxadiol | <1 | 2.5 | <1 | 2.8 |

Experimental Example A2

Analysis of Anticancer Effect

HepG2 (Human liver cancer cell line; KCLB-10023), A-549 (Human lung cancer cell line; KCLB-10185), P-388 (mouse lymph neoplasmic cell line; KCLB-10046) and L-1210 (mouse lymphocytic leukemia cell line; KCLB-10219) were each grown in RPMI 1640 medium supplemented with 10% FBS, 1% antibiotics-antimycotics (GIBCO, USA) and 2.2 g of $NaHCO_3$. Subsequently, HepG2 and A-549 cells were harvested by trypsinization (0.25% of trypsin) and each 180 μl of cells thereof was seeded into each well of a 96 well plate at 3×10⁴ cells/well. Then the plates were incubated for 24 hrs at 37° C. in 5% $CO_2$ incubator. For P-388 and L-1210 cells, each 180 μl of cells harvested by trypsinization (0.25% of trypsin) was seeded into each well of a 96 well plate at 4×10⁴ cells/well. Then the plates were incubated for 2 hrs at 37° C. in 5% $CO_2$ incubator. Butanol extracts of white ginseng and lactic acid bacteria fermented ginseng as in Table 3 were autoclaved and 20 μl of each was added to each well of 96 well plate prepared as described above at the concentration of 100 mg/ml. The 96 well plates were then incubated for 48 hrs at 37° C. in 5% $CO_2$ incubator. After 48 hrs, 20 mg/ml of MTT was added to each well of the 96 well plates and they were further incubated for 4 hrs in 5% $CO_2$ incubator. After 4 hrs, the media were removed from each well of the 96 well plates and 100 μl of DMSO was added thereto. Subsequently, the absorbance at 580 nm was determined for each well using ELISA reader to test for cell toxicity. The results obtained are shown in Table 3.

TABLE 3

| Type of ginseng | ED50(μg/ml) | | | |
| --- | --- | --- | --- | --- |
|  | P388 | L1210 | A549 | HepG2 |
| extract of regular ginseng | >100 | >100 | >100 | >100 |
| lactic acid bacteria-fermented product of white ginseng | 98 | 50 | 160 | 96 |
| lactic acid bacteria-fermented product of acid-treated ginseng | 82 | 51 | 102 | 95 |
| lactic acid bacteria-fermented product of high temperature treated ginseng | 78 | 45 | 87 | 91 |
| lactic acid bacteria-fermented product of pressurized ginseng | 85 | 52 | 105 | 92 |

Experimental Example A3

The Effect on *E. coli* HGU-3 and Harmful Intestinal Enzymes

Fermented ginseng products obtained from the examples above and 24 hr-cultivated *E. coli* HGU-3 (from Dong-Hyun Kim of School of Pharmacy, Kyunghee University, and properties are almost the same as those of *E. coli* in general.) together with each of *Bifidobacterium* KK-1 or *Bifidobacterium* KK-2 at the concentration of 10⁷ cells were inoculated into 5 ml of GAM solution and was incubated for 24 hrs. Subsequently the enzyme activities of β-glucuronidase and tryptophanase produced by bacterial strains, which are known as the cause for colon cancer and liver disorder, respectively, were measured.

The enzyme activity of β-glucuronidase was measured by adding 0.02 ml of 10 mM p-nitrophenyl-β-D-glucuronide and 0.1 ml of enzyme solution to 0.38 ml of 0.1M phosphate buffer (pH7.0) followed by an 1 hour incubation at 37° C. The reaction was then terminated by addition of 0.5 ml of 0.5N NaOH, and 1 ml of distilled water was added thereto followed by a centrifugation (2000×g, 20 min). Absorbance at 405 nm was then determined for each of the resulting supernatants.

The enzyme activity of tryptophanase was measured by adding 0.2 ml of complete reaction mixture (0.1M bicine, pH8.0, 4% pyridoxal-5-phosphate, 20% bovine serum albumin), 0.2 ml of 0.02M tryptophan and 0.1 ml of enzyme solution followed by a 30 min incubation. The reaction was then terminated by addition of 2 ml dye solution (p-dimethylaminobenzaldehyde 14.7 g, 95% ethanol 948 ml, C—$H_2SO_4$ 52 ml), and subsequently centrifuged at 2000×g for 20 min. Absorbance at 550 nm was then determined for each of the resulting supernatants.

The results obtained are shown in Table 4 and Table 5 for *Bifidobacterium* KK-1 and *Bifidobacterium* KK-2, respectively.

TABLE 4

| | % inhibition | |
| --- | --- | --- |
| | β-glucuronidase | tryptophanase |
| control (KK-1 and total intestinal flora cultivated in GAM) | 0 | 0 |
| ginseng extract (KK-1 and total intestinal flora cultivated in GAM containing 1% of ginseng extract) | 32 | 45 |
| lactic acid bacteria-fermented product of ginseng (KK-1 and total intestinal flora cultivated in GAM containing 1% of lactic acid bacteria-fermented product of ginseng) | 85 | 85 |
| lactic acid bacteria-fermented product of acid treated ginseng (KK-1 and total intestinal flora cultivated in GAM containing 1% of lactic acid bacteria fermented product of acid-treated ginseng) | 75 | 78 |
| lactic acid bacteria-fermented product of high temperature treated ginseng (KK-1 and total intestinal flora cultivated in GAM containing 1% of lactic acid bacteria fermented product of high temperature treated ginseng) | 89 | 87 |
| lactic acid bacteria-fermented product of pressurized ginseng (KK-1 and total intestinal flora cultivated in GAM containing 1% of lactic acid bacteria fermented product of pressurized ginseng) | 78 | 85 |

TABLE 5

| | % inhibition | |
|---|---|---|
| | β-glucuronidase | tryptophanase |
| control (KK-2 and total intestinal flora cultivated in GAM) | 0 | 0 |
| Ginseng extract (KK-2 and total intestinal flora cultivated in GAM containing 1% of ginseng extract) | 32 | 45 |
| lactic acid bacteria fermented product of ginseng (KK-2 and total intestinal flora cultivated in GAM containing 1% of lactic acid bacteria fermented product of ginseng) | 76 | 81 |
| lactic acid bacteria fermented product of acid treated ginseng (KK-2 and total intestinal flora cultivated in GAM containing 1% of lactic acid bacteria fermented product of acid-treated ginseng) | 67 | 88 |
| lactic acid bacteria fermented product of high temperature treated ginseng (KK-2 and total intestinal flora cultivated in GAM containing 1% of lactic acid bacteria fermented product of high temperature treated ginseng) | 82 | 68 |
| lactic acid bacteria fermented product of pressurized ginseng (KK-2 and total intestinal flora cultivated in GAM containing 1% of lactic acid bacteria fermented product of pressurized ginseng) | 71 | 78 |

It is known from Table 4 and 5 that the fermented ginseng products when absorbed into cells, have anticancer effect, suppress the activity of 13-glucurodinase and tryptophanase produced by intestinal bacteria, and thus have preventing effect on colon cancer and liver damage.

Example B1

1 g of *Panax quinquefolium* L. root as powdered (can contain 0.1 g of vitamin C) was suspended in 100 ml of milk. Yogurt was then obtained by inoculating each 1 ml (about $10^9$ cells/ml) of precultivated lactic acid bacteria *Lactobacillus bulgaricus, Streptococcus thermophilus* and *Bifidobacterium* KK-1 thereto, followed by a incubation for 24 hrs at 37.

Example B2

1 g of *Panax quinquefolium* L. root as powdered (can contain 0.1 g of vitamin C) was suspended in 100 ml of milk. Yogurt was then obtained by inoculating each 1 ml (about $10^9$ cells/ml) of precultivated *Lactobacillus bulgaricus, Streptococcus thermophilus* and *Bifidobacterium* KK-1 thereto, followed by a incubation for 24 hrs at 37° C.

Example B3

1 g of *Panax quinquefolium* L. root as dry-powdered (can contain 0.1 g of vitamin C) was suspended in 100 ml of milk. Yogurt was then obtained by inoculating each 1 ml (about $10^9$ cells/ml) of precultivated *Bifidobacterium* KK-1 and *Bifidobacterium* KK-2 thereto, followed by a incubation for 24 hrs at 37° C.

Example B4

*Panax quinquefolium* L. root as dry-powdered was suspended in water and lactic acid was added thereto at the final concentration of 1%. Then it was incubated at 60° C. for 5 hrs followed by a neutralization and drying. 1 g of powdered dry ginseng root (can contain 0.1 g of vitamin C) prepared as described above was suspended in 100 ml of milk. Yogurt was then obtained by inoculating each 1 ml (about $10^9$ cells/ml) of precultivated *Bifidobacterium* KK-1 and *Bifidobacterium* KK-11 thereto, followed by a incubation for 24 hrs at 37° C.

Example B5

1 g of *Panax quinquefolium* L. root as dry-powdered was moisturized and steamed for 2 hrs (can contain 0.1 g of vitamin C). And it was suspended in 100 ml of milk. Yogurt was then obtained by inoculating each 1 ml (about $10^9$ cells/ml) of precultivated *Bifidobacterium* KK-1 and *Bifidobacterium* KK-11 thereto, followed by a incubation for 24 hrs at 37° C.

Example B6

*Panax quinquefolium* L. root as dry-powdered (can contain 0.1 g of vitamin C) was pressurized for 2 hrs at 120° C. and 1 g thereof was suspended in 100 ml of milk. Yogurt was then obtained by inoculating each 1 ml (about $10^9$ cells/ml) of precultivated *Bifidobacterium* KK-1 and *Bifidobacterium* KK-11 thereto, followed by a incubation for 24 hrs at 37° C.

Example B7

*Panax quinquefolium* L. root as dry-powdered (can contain 0.1 g of vitamin C) was pressurized for 2 hrs at 120° C. and it was suspended in 100 ml of milk to give final concentration of 5%. Yogurt was then obtained by inoculating each 1 ml (about $10^9$ cells/ml) of precultivated *Bifidobacterium* KK-1 and *Bifidobacterium* KK-11 thereto, followed by a incubation for 24 hrs at 37° C.

Examples B8-B14

Each of lactic fermenting products of ginseng was obtained by repeating exactly the same process as examples B1 to B7 above, except 2 g (wet weight) of precultivated lactic acid bacteria and 100 ml of distilled water instead of 100 ml of milk were used.

Experiment Example B1

Content Analysis of Saponin Component 1 g of commercially available general *Panax quinquefolium* L. (4-yeared *Panax quinquefolium* L. root from Canada procured from Hongrim Trading Co., Ltd.) and each 1 g of its powdered dry, acid-treated, high temperature treated and pressurized version were individually mixed with 100 ml of milk containing 0.1 g of Vitamin C. Each of the above mixture was subsequently inoculated with 1 g of *Bifidobacterium* KK-1 and *Bifidobacterium* KK-11 and incubated for 72 hrs at 37° C. followed by a concentration by decompression to obtain fermented yogurt of dry *Panax quinquefolium* L., high temperature treated *Panax quinquefolium* L., acid-treated *Panax quinquefolium* L. and pressurized *Panax quinquefolium* L., respectively. Subsequently, *Panax quinquefolium* L. and its powdered dry, acid-treated, high temperature treated and pressurized version, and each of the fermented products above (2-20 g) were extracted with 100 ml of methanol 3 times. Each of the extracts was then concentrated and suspended in water followed by a extraction with 100 ml of ether 3 times. Each of the ether fractions was further extracted with 100 ml of butanol 3 times. The butanol fractions were then subject to concentration, and subsequent TLC analysis after dissolved in methanol (Solvent system: $CHCl_3$:MeOH:$H_2O$=65:35:10/$CHCl_3$:EtOAc:MeOH:$H_2O$=15:40:22:9; Spraying reagent: 5% sulfuric acid in methanol; TLC scanner: Shimadzu CS-9301 PC). The results are shown in Table 6.

The amount of saponin shown in the following table was calculated based on which is in 100% of the finally extracted fraction. The control contains exactly the same products as the experimental samples except containing no ginseng.

TABLE 6

| Name of the components | amount of chemical constituent(%) | | | |
|---|---|---|---|---|
| | *Panax quinquefolium* L. | fermented yogurt of *Panax quinquefolium* L. (example B3) | high temperature treated *Panax quinquefolium* L. | fermented yogurt of high temperature treated *Panax quinquefolium* L. (example B5) |
| ginsenoside Rb1 | 45.9 | 11.2 | 20.3 | 5.9 |
| ginsenoside Rb2 | 1.1 | <1 | <1 | <1 |
| ginsenoside Rc | 4.8 | <1 | 1.5 | <1 |
| ginsenoside Re | 23.6 | 12.3 | 9.9 | 3.5 |
| ginsenoside Rg3 | <1 | <1 | 19.1 | 4.6 |
| 20-ginsenoside Rg3 | <1 | <1 | 2.5 | <1 |
| compound K | 0 | 25.4 | <1 | 5.3 |
| ginsenoside Rh2 | <1 | <1 | <1 | 4.6 |
| $\Delta^{20}$-ginsenoside Rh2 | <1 | <1 | <1 | 1.2 |
| ginsenoside Rh1 | <1 | 2.8 | 4.8 | 1.8 |
| protopanaxadiol | <1 | <1 | <1 | <1 |

| Name of the components | amount of chemical constituent(%) | | | |
|---|---|---|---|---|
| | acid-treated *Panax quinquefolium* L. | fermented yogurt of acid-treated *Panax quinquefolium* L. (example B4) | pressurized *Panax quinquefolium* L. | fermented yogurt of pressurized *Panax quinquefolium* L. (example B6) |
| ginsenoside Rb1 | 4.5 | 1.4 | 11.8 | 3.2 |
| ginsenoside Rb2 | <1 | <1 | 1 | <1 |
| ginsenoside Rc | <1 | <1 | <1 | <1 |
| ginsenoside Re | 6.8 | 4.2 | 9.3 | 3.1 |
| ginsenoside Rg3 | 28 | 11.5 | 23.2 | 9.6 |
| 20-ginsenoside Rg3 | 2.5 | <1.1 | 6.5 | 3.1 |
| compound K | 0 | 2.8 | 0 | 3.7 |
| ginsenoside Rh2 | 0.2 | 11.3 | <1 | 8.6 |
| $\Delta^{20}$-ginsenoside Rh2 | 0.1 | 1.4 | <1 | 1.1 |
| ginsenoside Rh1 | 1.5 | 3.7 | 1.2 | 2.5 |
| protopanaxadiol | <1 | <1 | <1 | 1.4 |

Experimental Example B2

Analysis of Anticancer Effect

HepG2 (Human liver cancer cell line; KCLB-10023), A-549 (Human lung cancer cell line; KCLB-10185), P-388 (mouse lymph neoplasmic cell line; KCLB-10046), L-1210 (mouse lymphocytic leukemia cell line; KCLB-10219) were each grown in RPMI 1640 medium supplemented with 10% FBS, 1% antibiotics-antimycotics (GIBCO, USA) and 2.2 g of $NaHCO3$. Subsequently, HepG2 and A-549 cells were harvested by trypsinization (0.25% of trypsin) and each 18019 of cells thereof was seeded into each well of a 96 well plate at $3\times10^4$ cells/well. Then the plates were incubated for 24 hrs at 37° C. in 5% $CO_2$ incubator. For P-388 and L-1210 cells, each 180 µl of cells harvested by trypsinization (0.25% of trypsin) was seeded into each well of a 96 well plate at $4\times10^4$ cells/well. Then the plates were incubated for 2 hrs at 37° C. in 5% $CO_2$ incubator. *Panax quinquefolium* L. extracts and lactic fermenting products of ginseng prepared as in Table 3 (Butanol extracted fraction after fermented with lactic acid bacteria) were autoclaved and 20 μl of each was added to each well of 96 well plate as described above at the concentration of 10 mg/ml. The 96 well plates were then incubated for 48 hrs at 37° C. in 5% $CO_2$ incubator. After 48 hrs, 20 mg/ml of MTT was added to each well and further incubated for 4 hrs in 5% $CO_2$ incubator. After 4 hrs, the media were removed from each well of the 96 well plates and 100 μl of DMSO was added thereto. Subsequently, the absorbance at 580 nm was determined for each well using ELISA reader to test for cell toxicity. The results obtained are shown in Table 7.

TABLE 7

| Type of ginseng | ED50(μg/ml) | | | |
| --- | --- | --- | --- | --- |
| | P388 | L1210 | A549 | HepG2 |
| Extract of regular *Panax quinquefolium* L. | >100 | >100 | >100 | >100 |
| lactic fermenting products of *Panax quinquefolium* L. | 78 | 65 | >100 | 89 |
| lactic fermenting products of acid-treated *Panax quinquefolium* L. | 89 | 65 | 95 | 85 |
| lactic fermenting products of high temperature treated *Panax quinquefolium* L. | 92 | 50 | 89 | 95 |
| lactic fermenting products of pressurized *Panax quinquefolium* L. | 92 | 60 | 110 | 95 |

Experimental Example B3

The Effect on *E. coli* HGU-3 and Harmful Intestinal Enzymes 24 hr-cultivated *E. coli* HGU-3 (from Dong-Hyun Kim of School of Pharmacy, Kyunghee University and properties are almost the same as those of *E coli* in general.) (or freshly prepared total intestinal flora of human) together with each of *Bifidobacterium* KK-1 (or *Bifidobacterium* KK-2 or *Bifidobacterium* H-1 or *Bifidobacterium* KK-11) at the concentration of $10^5$ cells were inoculated into 5 ml of GAM solution (the one before this contains ginseng; no ginseng) and it was incubated for 24 hrs. The enzyme activity of β-glucuronidase and tryptophanase produced by bacterial strains, which are known as the cause for colon cancer and liver disorder, respectively, were measured.

The enzyme activity of β-glucuronidase was measured by adding 0.02 ml of 10 mM p-nitrophenyl-β-D-glucuronid and 0.1 ml of enzyme solution to 0.38 ml of 0.1M phosphate buffer (pH7.0) followed by 1 hour incubation at 37° C. The reaction was then terminated by addition of 0.5 ml of 0.5N NaOH and 1 ml of distilled water was added thereto followed by a centrifugation (2000×g, 20 min). Absorbance at 405 nm was then determined for each of the resulting supernatants.

The enzyme activity of tryptophanase was measured by adding 0.2 ml of complete reaction mixture (0.1M bicine, pH8.0, 4% pyridoxal-5-phosphate, 20% bovine serum albumin), 0.2 ml of 0.02M tryptophan, 0.1 ml of enzyme solution followed by a 30 min incubation. The reaction was then terminated by addition of 2 ml dye solution (p-dimethylaminobenzaldehyde 14.7 g, 95% ethanol 948 ml, $C-H_2SO_4$ 52 ml), and subsequently centrifuged at 2000×g for 20 min. Absorbance at 550 nm was then determined for each of the resulting supernatants.

The quantitative analysis of ammonia produced was done by adding 0.1M phosphate buffer (pH7.0), 20 μl of fractional suspension and 100 μl of 1N $H_2SO_4$, and adding each 1 ml of solution mixture 1 (1% propanol, 0.005% sodium nitroprusside) and solution mixture 2 (0.1% sodium hypochlorite, 0.5% sodium hydroxide, 5.5% sodium phosphate dibasic) thereto followed by a heating at 60° C. for 20 min and subsequent cooling to room temperature. The absorbance at 660 nm was then determined.

The results obtained are shown in Table 8 where the inhibitory effects on the activity of colon cancer causing enzymes are shown for the mixed culture of *E. coli* HUG-3 and lactic acid bacteria, and that of total intestinal flora of human and lactic acid bacteria (control contains only *E. coli* HUG-3).

TABLE 8

| | % inhibition | | |
| --- | --- | --- | --- |
| | β-glucurodinase | trypto-phanase | production of ammonia |
| control | 0 | 0 | 0 |
| *Bifidobacterium* KK-1 | 85 | 78 | 67 |
| *Bifidobacterium* KK-2 | 70 | 89 | 75 |
| *Bifidobacterium* H-1 | 32 | 45 | 59 |
| *Bifidobacterium* KK-11 | 68 | 75 | 69 |

It is known from Table 8 that the fermented products of ginseng, when absorbed into cells, have anticancer effect, and suppress the activity of β-glucurodinase and tryptophanase produced by intestinal bacteria and also the production of ammonia, thus have preventing effect on colon cancer and liver damage.

Experimental Example B4

Suppression Effect on the Growth *E. coli* 0157

The suppression effect of lactic acid bacteria from fermented ginseng on the growth of *E. coli* 0157 was investigated. *E. coli* 0157 was inoculated into each 5 ml of GAM at the concentration of $10^5$/ml. Each of the culture above was then mixed with each of the lactic acid bacteria listed in Table 9 at the ratio of 1:1 and 1:10 (*E. coli* 0157 to lactic acid bacteria). The mixed culture was then incubated for 20 hrs at 37° C. and subsequently streaked on a TS agar plate, followed by a incubation at 37° C. for 20 hrs. The *E. coli* 0157 colonies on the agar plate were counted thereafter.

TABLE 9

| | % inhibition | |
| --- | --- | --- |
| | 1(harmful bacteria $10^5$/ml):1(lactic acid bacteria $10^5$/ml) | 1(harmful bacteria $10^5$/ml):10(lactic acid bacteria $10^6$/ml) |
| Control (harmful bacteria only) | 0 | 0 |
| *Bifidobacterium* KK-1 and harmful bacteria | 82 | 95 |
| *Bifidobacterium* KK-2 and harmful bacteria | 80 | 85 |
| *Bifidobacterium* H-1 and harmful bacteria | 78 | 88 |
| *Bifidobacterium* KK-11 and harmful bacteria | 67 | 85 |

INDUSTRIAL APPLICABILITY

As shown above, fermented products of ginseng containing *Panax quiquefolium* L. and *Panax quinquefolium* L. according to the present invention contain large amount of compound K, Ginsenoside Rh1 and Rh2, and $\Delta^{20}$-ginsenoside Rh2 which are almost not present, or if any, only in extremely small quantities in unprocessed ginseng. As a result, it can be suggested that the fermented products of ginseng not only have anticancer and anti-allergenic effect but also improve intestinal environment. Furthermore, it has the strong effect of preventing colon cancer, protecting from liver damage and suppressing the growth of harmful intestinal bacteria. Therefore, yogurt containing the fermented product(s) of ginseng as an active component should prove industrially or commercially useful as a yogurt with specific function providing the above mentioned physiological activities of Saponin.

What is claimed is:

1. A lactic fermentation product of ginseng prepared by fermenting ginseng with lactic acid bacteria capable bio-converting ingredient of ginsenosides, wherein said lactic acid bacteria is bifidobacterium KK-1 Accession Number (KCCM-10364), and wherein the total amount of (Compound K+ginsenoside Rh1), (ginsenoside Rh1+ginsenoside Rh2), (ginsenoside Rh2+$\Delta^{20}$-ginsenoside Rh2+ginsenoside Rh1) or (Compound K+ginsenoside Rh1+ginsenoside Rh2) is respectively in the ratio of more than 0.1 with respect to the amount of (ginsenoside Rc+ginsenoside Rd+ginsenoside Rb1+ginsenoside Rb2+ginsenoside Re+ginsenoside Rg1).

2. A lactic fermentation product of ginseng as claimed in claim 1 wherein said ginseng is selected from the group consisting of dry ginseng powder, ginseng treated by acid, ginseng treated by heat and ginseng treated under pressure.

3. A ginseng yoghurt comprising the fermentation product of ginseng prepared by fermenting ginseng with lactic acid bacteria capable of bio-converting ingredients of ginsenosides, wherein said lactic acid bacteria is bifidobacterium KK-1 Accession No. (KCCM-10364), and wherein the total amount of (Compound K+ginsenoside Rh1), (ginsenoside Rh1+ginsenoside Rh2), (ginsenoside Rh2+$\Delta^{20}$-ginsenoside Rh2+ginsenoside Rh1) or (Compound K+ginsenoside Rh1+ginsenoside Rh2) is respectively in the ratio of more than 0.1 with respect to the amount of (ginsenoside Rc+ginsenoside Rd+ginsenoside Rb1+ginsenoside Rb2+ginsenoside Re+ginsenoside Rg1).

4. The ginseng yoghurt as claimed in claim 3 wherein the fermentation product of ginseng is incorporated into said ginseng yoghurt through the fermentation process wherein both milk and ginseng are fermented together.

5. Bifidobacterium KK-1 Accession Number (KCCM-10364).

* * * * *